US011096927B2

(12) United States Patent
Tang et al.

(10) Patent No.: US 11,096,927 B2
(45) Date of Patent: Aug. 24, 2021

(54) ANTI-FLAVIVIRUS COMPOUNDS AND METHODS OF USE

(71) Applicants: FLORIDA STATE UNIVERSITY RESEARCH FOUNDATION, INC., Tallahassee, FL (US); The United States of America, as represented by the Secretary, Department of Health and Human Services, Bethesda, MD (US); THE TRUSTEES OF THE UNIVERSITY OF PENNSYLVANIA, Philadelphia, PA (US)

(72) Inventors: Hengli Tang, Tallahassee, FL (US); Emily M. Lee, Tallahassee, FL (US); Wei Zheng, Rockville, MD (US); Ruili Huang, Rockville, MD (US); Miao Xu, Rockville, MD (US); Wenwei Huang, Rockville, MD (US); Khalida Shamim, Rockville, MD (US); Guoli Ming, Philadelphia, PA (US); Hongjun Song, Philadelphia, PA (US)

(73) Assignees: FLORIDA STATE UNIVERSITY RESEARCH FOUNDATION, INC., Tallahassee, FL (US); THE UNITED STATES OF AMERICA, AS REPRESENTED BY THE SECRETARY, DEPARTMENT OF HEALTH AND HUMAN SERVICES, Bethesda, MD (US); THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 16/721,221

(22) Filed: Dec. 19, 2019

(65) Prior Publication Data
US 2020/0197369 A1 Jun. 25, 2020

Related U.S. Application Data

(60) Provisional application No. 62/781,687, filed on Dec. 19, 2018.

(51) Int. Cl.
| | |
|---|---|
| *A61P 31/14* | (2006.01) |
| *A61K 31/165* | (2006.01) |
| *A61K 31/4184* | (2006.01) |
| *A61K 31/245* | (2006.01) |
| *A61K 31/433* | (2006.01) |
| *A61K 31/4535* | (2006.01) |
| *A61K 31/4162* | (2006.01) |
| *A61K 31/517* | (2006.01) |
| *A61K 31/4741* | (2006.01) |
| *A61K 31/554* | (2006.01) |
| *A61K 31/422* | (2006.01) |
| *A61K 31/4709* | (2006.01) |
| *A61K 31/336* | (2006.01) |
| *A61K 31/427* | (2006.01) |
| *A61K 31/506* | (2006.01) |
| *A61K 31/519* | (2006.01) |
| *A61K 31/352* | (2006.01) |

(52) U.S. Cl.
CPC ........ *A61K 31/4184* (2013.01); *A61K 31/165* (2013.01); *A61K 31/245* (2013.01); *A61K 31/336* (2013.01); *A61K 31/352* (2013.01); *A61K 31/4162* (2013.01); *A61K 31/422* (2013.01); *A61K 31/427* (2013.01); *A61K 31/433* (2013.01); *A61K 31/4535* (2013.01); *A61K 31/4709* (2013.01); *A61K 31/4741* (2013.01); *A61K 31/506* (2013.01); *A61K 31/517* (2013.01); *A61K 31/519* (2013.01); *A61K 31/554* (2013.01); *A61P 31/14* (2018.01)

(58) Field of Classification Search
CPC ......... A61K 31/165; A61P 31/14; A61P 31/12
See application file for complete search history.

(56) References Cited

U.S. PATENT DOCUMENTS

| | | | |
|---|---|---|---|
| 8,415,395 | B1 | 4/2013 | Davis et al. |
| 8,779,156 | B2 | 7/2014 | Das et al. |
| 10,555,942 | B2 | 2/2020 | Tang et al. |
| 2014/0243257 | A1 | 8/2014 | Henderson et al. |
| 2015/0152064 | A1 | 6/2015 | Einav et al. |
| 2015/0164910 | A1 | 6/2015 | Krogstad et al. |
| 2020/0121672 | A1 | 4/2020 | Tang et al. |
| 2020/0164051 | A1 | 5/2020 | Tang et al. |

FOREIGN PATENT DOCUMENTS

| | | |
|---|---|---|
| WO | WO 2018/017426 | 1/2018 |
| WO | WO 2019/075011 | 4/2019 |

OTHER PUBLICATIONS

Acosta et al. Journal of General Virology, 2008, vol. 89, pp. 474-484 (Year: 2008).*

(Continued)

*Primary Examiner* — James D. Anderson
(74) *Attorney, Agent, or Firm* — Saliwanchik, Lloyd & Eisenschenk

(57) ABSTRACT

The present invention concerns the use of compounds and compositions for the treatment or prevention of Flavivirus infections, such as dengue virus infections and Zika virus infections. Aspects of the invention include methods for treating or preventing Flavivirus virus infection, such as dengue virus and Zika virus infection, by administering a compound or composition of the invention, to a subject in need thereof; methods for inhibiting Flavivirus infections, such as dengue virus and Zika virus infections, in a cell in vitro or in vivo; pharmaceutical compositions; packaged dosage formulations; and kits useful for treating or preventing Flavivirus infections, such as dengue virus and Zika virus infections.

19 Claims, No Drawings

(56) References Cited

OTHER PUBLICATIONS

Akodad et al. Archives of Cardiovascular Disease, 2017, vol. 110, pp. 395-402 (Year: 2017).*
Gabrielsen et al. Journal of Natural Products, 1992, vol. 55, No. 11, pp. 1569-1581 (Year: 1992).*
Araujo, L.M. et al. "Guillain-Barré syndrome associated with the Zika virus outbreak in Brazil" *Arq. Neuropsiquiatr.*, 2016, 74(3):253-255.
Berge, S. et al. "Pharmaceutical Salts" *J. Pharmaceut. Sci.*, 1977, 66(1):1-19.
Cao-Lormeau, V-M. et al. "Zika Virus, French Polynesia, South Pacific, 2013" *Emerging Infectious Diseases*, 2014, 20(6):1085-1086.
Cao-Lormeau, V-M. et al. "Guillain-Barré Syndrome outbreak caused by Zika virus infection in French Polynesia" *Lancet*, 2016, 387(10027):1531-1539.
Dick, G.W.A. et al. "Zika Virus. (I). Isolations and Serological Specificity" *Trans. Royal Soc. Trop. Med. Hyg.*, 1952, 46(5):509-520.
Duffy, M. et al. "Zika Virus Outbreak on Yap Island, Federated States of Micronesia" *New Eng. J. Med.*, 2009, 360:2536-2543.
Fatima, A. and Wang, J. "Progress in the Diagnosis of Dengue Virus Infections and Importance of Point of Care Test: A Review" *Pak. J. Pharm. Sci.*, 2015, 28(1):271-280.
Gourinat, A-C. et al. "Detection of Zika Virus in Urine" *Emerging Infectious Diseases*, 2015, 21(1):84-86.
Heymann, D. et al. "Zika virus and microcephaly: why is this situation a PHEIC?" *Lancet*, 2016, 387:719-721.
Huhtamo, E. et al. "Early diagnosis of dengue in travelers: Comparison of a novel real-time RT-PCR, NS1 antigen detection and serology" *J. Clin. Virol.*, 2010, 47:49-53.
Kuno, G. et al. "Phylogeny of the Genus *Flavivirus*" *J. Viro.*, 1998, 72(1):73-83.
Mlakar, J. et al. "Zika Virus Associated with Microcephaly" *New Eng. J. Med.*, 2016, 374:951-958.
Muller, D. et al. "Clinical and Laboratory Diagnosis of Dengue Virus Infection" *J. Infectious Dis.*, 2017, 215(S2):S89-S95.
Musso, D. et al. "Detection of Zika virus in saliva" *J. Clin. Virol.*, 2015, 68:53-55.
Mustafa, M.S. et al. "Discovery of fifth serotype of dengue virus (DENV-5): A new public health dilemma in dengue control" *Med. J. Armed Forces India*, 2015, 71:67-70.
Nguyen, N. et al. "Diagnostic Performance of Dengue Virus Envelope Domain III in Acute Dengue Infection" *Int'l J. Mol. Sci.*, 2019, 20:3464 (16 pages).
Pang, J. et al. "Progress and Challenges towards Point-of-Care Diagnostic Development for Dengue" *J. Clin. Microbiol.*, 2017, 55:3339-3349.
Parkash, O. and Shueb, R. "Diagnosis of Dengue Infection Using Conventional and Biosensor Based Techniques" *Viruses*, 2015, 7:5410-5427.
Rasmussen, S. et al. "Zika Virus and Birth Defects—Reviewing the Evidence for Causality" *New Eng. J. Med.*, 2016, 374(20):1981-1987.
Wu, K-M. "A New Classification of Prodrugs: Regulatory Perspectives" *Pharmaceut.*, 2009, 2:77-81.

* cited by examiner

ANTI-FLAVIVIRUS COMPOUNDS AND METHODS OF USE

CROSS-REFERENCE TO RELATED APPLICATION

The present application claims the benefit of U.S. Provisional Application Ser. No. 62/781,687, filed Dec. 19, 2018, which is hereby incorporated by reference herein in its entirety, including any figures, tables, nucleic acid sequences, amino acid sequences, or drawings.

BACKGROUND OF THE INVENTION

Flaviviruses are a genus within the Flaviviridae family with a single-stranded, positive-sense RNA genome. Many representatives of the genus, such as Dengue virus (DENV), West Nile virus (WNV), Zika viruses (ZIKV), tick-borne encephalitis virus, and yellow fever virus, are associated with pathogenic effects in humans. Currently, approved treatments for DENV or ZIKV infection are supportive, but not anti-viral.

ZIKV, a mosquito-borne flavivirus, has re-emerged and spread across the Western Hemisphere in the past year. First isolated in 1947 from a sentinel rhesus macaque in the Zika Forest region of Uganda [1], ZIKV had remained in relative obscurity for many years until outbreaks in the Pacific islands and then the Americas in the past decade [2-4]. A large outbreak started in Brazil in late 2014 and is a growing public health concern [5]. Currently, active transmission has been reported in 58 countries and territories globally. About 20% of ZIKV infected individuals develop symptoms, which mostly resemble symptoms caused by other arboviruses, such as dengue viruses or chikungunya virus. Unlike these viruses, however, ZIKV causes congenital defects, including microcephaly [6,7], and is also associated with Guillain-Barré syndrome in infected adults [8,9].

DENV, the cause of dengue fever, has increased dramatically in recent decades, becoming one of the most impactful mosquito-borne human pathogens posing a threat to tropical countries and their visitors. Dengue disease is a global public health threat caused by the spread of four antigenically distinct serotypes of DENV (DENV-1, -2, -3, and -4). Dengue disease can range in severity from mild dengue fever to severe, life-threatening syndromes, dengue hemorrhagic fever (DHF), and dengue shock syndrome (DSS). Infection by one type of DENV can provide immunity against that specific serotype, but a subsequent infection by any of the other serotypes of the virus increases the risk of developing severe dengue disease, DHF, and DSS. There is currently no specific treatment for dengue disease, and most forms of therapy are supportive in nature.

BRIEF SUMMARY OF THE INVENTION

A computational model has been developed based on data from the flavivirus Zika NS-1 assay and was used to predict new anti-Flavivirus compounds. Because the NS-1 protein is synthesized only in the flavivirus replication stage, the inhibition of NS-1 protein level by compounds determined in this NS-1 assay, indicates the inhibition of virus replication in human cells. The model identified 19 compounds that were also experimentally verified to be active and potent in inhibiting NS-1 production and blocking viral replication in human cells. These compounds may be used in new therapies for the treatment of infection with flaviviruses, such as Zika virus and dengue virus.

The invention concerns compounds selected from the group consisting of NCGC00102779-01, NCGC00113159-01, NCGC00104879-01, NCGC00025125-18, NCGC00018238-09, NCGC00112058-01, NCGC00169957-03, NCGC00387651-01, NCGC00179895-03, NCGC00108525-01, NCGC00071621-03, NCGC00131231-01, NCGC00246910-02, NCGC00108581-01, NCGC00107055-01, NCGC00263862-02, NCGC00072088-02, NCGC00357393-02, and NCGC00378623-01 (the chemical structures of which are shown in Table 1), or a prodrug, metabolite, or derivative of any of the foregoing, or a pharmaceutically acceptable salt of any of the foregoing.

Another aspect of the invention is a composition comprising at least one compound selected from the group consisting of:
NCGC00102779-01, NCGC00113159-01, NCGC00104879-01, NCGC00025125-18, NCGC00018238-09, NCGC00112058-01, NCGC00169957-03, NCGC00387651-01, NCGC00179895-03, NCGC00108525-01, NCGC00071621-03, NCGC00131231-01, NCGC00246910-02, NCGC00108581-01, NCGC00107055-01, NCGC00263862-02, NCGC00072088-02, NCGC00357393-02, and NCGC00378623-01, or a prodrug, metabolite, or derivative of any of the foregoing, or a pharmaceutically acceptable salt of any of the foregoing; and a pharmaceutically acceptable carrier or diluent.

Another aspect of the invention concerns a method for treating or preventing flavivirus infection in a human or non-human animal subject in need thereof, the method comprising administering to the subject an effective amount of at least one compound selected from the group consisting of:
NCGC00102779-01, NCGC00113159-01, NCGC00104879-01, NCGC00025125-18, NCGC00018238-09, NCGC00112058-01, NCGC00169957-03, NCGC00387651-01, NCGC00179895-03, NCGC00108525-01, NCGC00071621-03, NCGC00131231-01, NCGC00246910-02, NCGC00108581-01, NCGC00107055-01, NCGC00263862-02, NCGC00072088-02, NCGC00357393-02, and NCGC00378623-01, or a prodrug, metabolite, or derivative of any of the foregoing, or a pharmaceutically acceptable salt of any of the foregoing; or a composition comprising at least one of the aforementioned compounds, and pharmaceutically acceptable carrier or diluent.

Another aspect of the invention is a method for inhibiting flavivirus infection in human or non-human animal cells in vitro or in vivo, the method comprising contacting an effective amount of at least one compound to a human or non-human animal cell in vitro or in vivo before or after exposure of the cell to flavivirus, wherein the compound is selected from the group consisting of:
NCGC00102779-01, NCGC00113159-01, NCGC00104879-01, NCGC00025125-18, NCGC00018238-09, NCGC00112058-01, NCGC00169957-03, NCGC00387651-01, NCGC00179895-03, NCGC00108525-01, NCGC00071621-03, NCGC00131231-01, NCGC00246910-02, NCGC00108581-01, NCGC00107055-01, NCGC00263862-02, NCGC00072088-02, NCGC00357393-02, and NCGC00378623-01, or a prodrug, metabolite, or derivative of any of the foregoing, or a pharmaceutically acceptable salt of any of the foregoing; or a composition comprising at least one of the aforementioned compounds, and pharmaceutically acceptable carrier or diluent.

Another aspect of the invention concerns a packaged dosage formulation comprising at least one anti-flavivirus one compound in a pharmaceutically acceptable dosage in one or more packages, packets, or containers.

Another aspect of the invention concerns a kit comprising, in one or more containers, at least one anti-flavivirus compound.

DETAILED DESCRIPTION OF THE INVENTION

The flavivirus NS-1 protein is only expressed during the virus replication stage. The inventors identified several compounds that inhibited NS-1 production in human cells. These compounds block flavivirus virus replication and thus may be used as anti-flavivirus agents to inhibit flavivirus infections, such as dengue virus (DENV), West Nile virus (WNV), Zika viruses (ZIKV), tick-borne encephalitis virus, and yellow fever virus, and others.

An aspect of the invention includes the compounds selected from the group consisting of NCGC00102779-01, NCGC00113159-01, NCGC00104879-01, NCGC00025125-18, NCGC00018238-09, NCGC00112058-01, NCGC00169957-03, NCGC00387651-01, NCGC00179895-03, NCGC00108525-01, NCGC00071621-03, NCGC00131231-01, NCGC00246910-02, NCGC00108581-01, NCGC00107055-01, NCGC00263862-02, NCGC00072088-02, NCGC00357393-02, and NCGC00378623-01, or a prodrug, metabolite, or derivative of any of the foregoing, or a pharmaceutically acceptable salt of any of the foregoing.

The chemical structures of NCGC00102779-01, NCGC00113159-01, NCGC00104879-01, NCGC00025125-18, NCGC00018238-09, NCGC00112058-01, NCGC00169957-03, NCGC00387651-01, NCGC00179895-03, NCGC00108525-01, NCGC00071621-03, NCGC00131231-01, NCGC00246910-02, NCGC00108581-01, NCGC00107055-01, NCGC00263862-02, NCGC00072088-02, NCGC00357393-02, and NCGC00378623-01 are shown in Table 1.

TABLE 1

| | Sample ID and IUPAC Name | Structure |
|---|---|---|
| 1 | NCGC00018238-09<br>methyl (6-propoxy-1H-benzo[d]imidazol-2-yl)carbamate | 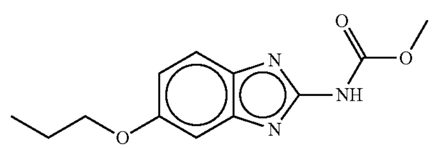 |
| 2 | NCGC00025125-18<br>N-[(7S)-1,2,3,10-tetramethoxy-9-oxo-6,7-dihydro-5H-benzo[a]heptalen-7-yl]acetamide | 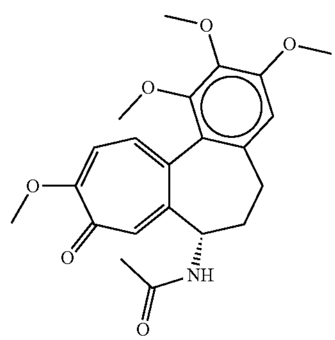 |
| 3 | NCGC00071621-03<br>4-(3-(2-methoxyphenyl)-[1,2,4]triazolo[3,4-b][1,3,4]thiadiazol-6-yl)-N,N-dimethylaniline | 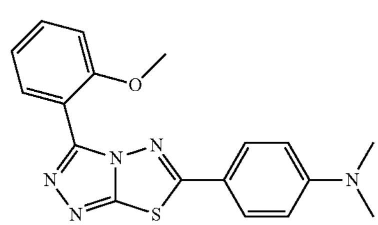 [SMILES: COc1ccccc1-c1nnc2sc(-c3ccc(N(C)C)cc3)nn12] |
| 4 | NCGC00072088-02<br>N-(pyridin-3-yl)thiophene-2-carboxamide | 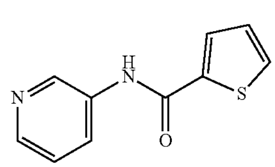 [SMILES: O=C(Nc1cccnc1)c1cccs1] |

TABLE 1-continued

| Sample ID and IUPAC Name | Structure |
|---|---|
| 5 NCGC00102779-01<br>5-(4-ethoxyphenyl)-4-(3-fluorophenyl)-3-(thiophen-2-yl)-4,5-dihydropyrrolo[3,4-c]pyrazol-6(1H)-one | |
| 6 NCGC00104879-01<br>N-(2-chlorobenzyl)-3-(2-methoxyethyl)-2,4-dioxo-1,2,3,4-tetrahydroquinazoline-7-carboxamide | |
| 7 NCGC00107055-01<br>9-(3-bromo-4,5-dimethoxyphenyl)-2,3,8,9-tetrahydro-[1,4]dioxino[2,3-g]quinolin-7(6H)-one | |
| 8 NCGC00108525-01<br>ethyl 4-(3-(4-methoxyphenyl)-6-oxo-4-(p-tolyl)-4,6-dihydropyrrolo[3,4-c]pyrazol-5(1H)-yl)benzoate | |
| 9 NCGC00108581-01<br>ethyl 4-(3-(furan-2-yl)-6-oxo-4-(p-tolyl)-4,6-dihydropyrrolo[3,4-c]pyrazol-5(1H)-yl)benzoate | |
| 10 NCGC00112058-01<br>N-(2-chlorobenzyl)-1,4,11-trimethyldibenzo[b,f][1,4]thiazepine-8-carboxamide | |

TABLE 1-continued

| Sample ID and IUPAC Name | Structure |
| --- | --- |
| 11 NCGC00113159-01<br>methyl 4-[[5-methyl-2-(4-methylphenyl)-1,3-oxazol-4-yl]methyl]furo[3,2-b]pyrrole-5-carboxylate | |
| 12 NCGC00131231-01<br>4-(tert-butyl)-N-(1-(thiophene-2-carbonyl)-1,2,3,4-tetrahydroquinolin-6-yl)benzamide | |
| 13 NCGC00169957-03<br>3-(sec-butyl)-16-isobutyl-6-isopropyl-5,8,9-trimethyldodecahydropyrrolo[1,2-d][1]oxa[4,7,10,13,16]pentaazacyclo-nonadecine-1,4,7,10,14,17(11H,16H)-hexaone | |
| 14 NCGC00179895-03<br>((2S,2'R,3'R,4'S,5'S,5a'R,9a'R)-4'-acetoxy-3'-hydroxy-5',8'-dimethyl-2',3',4',5',7',9a'-hexahydrospiro[oxirane-2,10'-[2,5]methanobenzo[b]oxepin]-5a'(6'H)-yl)methyl acetate | |

TABLE 1-continued

| Sample ID and IUPAC Name | Structure |
|---|---|
| 15 NCGC00246910-02<br>7-(3,4-dihydroxy-5-(hydroxymethyl)tetrahydrofuran-2-yl)-1,7-dihydro-4H-pyrrolo[2,3-d]pyrimidin-4-one | |
| 16 NCGC00263862-02<br>5-fluoro-1-((4R,5R)-4-hydroxy-5-(hydroxymethyl)tetrahydrofuran-2-yl)pyrimidine-2,4(1H,3H)-dione | |
| 17 NCGC00357393-02<br>(2S,3R,4S,4aR)-2,3,4,7-tetrahydroxy-3,4,4a,5-tetrahydro-[1,3]dioxolo[4,5-j]phenanthridin-6(2H)-one | |
| 18 NCGC00378623-01<br>(S)-2-((S)-2-(dimethylamino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethylbutanamide | |
| 19 NCGC00387651-01<br>(2S,2'R,3'R,4'S,5'S,5a'R,7'S,9a'R)-4'-acetoxy-5a'-(acetoxymethyl)-3'-hydroxy-5',8'-dimethyl-2',3',4',5',5a',6',7',9a'-octahydrospiro[oxirane-2,10'-[2,5]methanobenzo[b]oxepin]-7'-yl 3-methylbutanoate | |

Another aspect of the invention includes a composition comprising a compound selected from the group consisting of:
NCGC00102779-01,
NCGC00104879-01,
NCGC00018238-09,
NCGC00169957-03,
NCGC00179895-03,
NCGC00071621-03,
NCGC00246910-02,
NCGC00107055-01,
NCGC00072088-02,
NCGC00113159-01,
NCGC00025125-18,
NCGC00112058-01,
NCGC00387651-01,
NCGC00108525-01,
NCGC00131231-01,
NCGC00108581-01,
NCGC00263862-02,
NCGC00357393-02, and NCGC00378623-01, or a prodrug, metabolite, or derivative of any of the foregoing, or a pharmaceutically acceptable salt of any of the foregoing; and a pharmaceutically acceptable carrier or diluent. The composition may include one, two or more compounds of the foregoing compounds. Optionally, the composition may include one or more additional biologically active agents, such as an additional agent useful for the treatment or prevention of a flavivirus infection.

Another aspect of the invention is a method for treating or preventing flavivirus infection in a human or non-human animal subject in need thereof, the method comprising administering to the subject an effective amount of at least one compound selected from the group consisting of: NCGC00102779-01, NCGC00113159-01, NCGC00104879-01, NCGC00025125-18, NCGC00018238-09, NCGC00112058-01, NCGC00169957-03, NCGC00387651-01, NCGC00179895-03, NCGC00108525-01, NCGC00071621-03, NCGC00131231-01, NCGC00246910-02, NCGC00108581-01, NCGC00107055-01, NCGC00263862-02, NCGC00072088-02, NCGC00357393-02, and NCGC00378623-01, or a prodrug, metabolite, or derivative of any of the foregoing, or a pharmaceutically acceptable salt of any of the foregoing; or a composition comprising at least one of the aforementioned compounds, and pharmaceutically acceptable carrier or diluent. In some embodiments, two or more of the aforementioned compounds are administered, within the same formulation, or separate formulations.

In some embodiments, the flavivirus infection is a Zika virus infection. In some embodiments, the flavivirus infection is a dengue virus infection. The DENV may be any type. For example, the DENV may be any of serotypes DENV-1, -2, -3, or -4, which follow the human cycle, or DENV-5, which follows the sylvatic cycle (Mustafa Lt Col M S et al., *Medical Journal Armed Forces India*, 2015, 71:67-70).

The compounds and compositions may be administered as a therapy, wherein the subject has the flavivirus infection at the time the compound or composition is administered, or the compound or composition may be administered as prophylaxis, to prevent or delay onset of the flavivirus infection, wherein the subject does not have the flavivirus infection at the time the compound or composition is administered.

Optionally, for therapy, the method may include the step of identifying the subject as having the flavivirus infection, before administering the compound or composition. Subjects with a flavivirus infection may be identified by methods known in the art, such as by assaying a biological sample (e.g., blood, serum, or plasma) obtained from the subject for the presence of flavivirus nucleic acids or flavivirus proteins. Such assays may involve, for example, the use of reverse transcriptase-polymerase chain reaction (RT-PCR), immunological assay, or Plaque-reduction neutralization testing (PRNT).

The compounds and compositions may be administered by any effective method. In some embodiments, the compounds and compositions are administered orally, nasally, rectally, parenterally, subcutaneously, intramuscularly, or intravascularly.

Optionally, the method may further include administering one or more additional biologically active agents, such as additional agents for treating or preventing flavivirus infection, or a symptom thereof, in the same formulation as the aforementioned anti-flavivirus compound, or in a separate formulation before, during, or after administration of the anti-flavivirus compound.

Another aspect of the invention is a method for inhibiting flavivirus infection in human or non-human animal cells in vitro or in vivo, the method comprising contacting an effective amount of at least one compound to a human or non-human animal cell in vitro or in vivo before or after exposure of the cell to flavivirus, wherein the compound is selected from the group consisting of: NCGC00102779-01, NCGC00113159-01, NCGC00104879-01, NCGC00025125-18, NCGC00018238-09, NCGC00112058-01, NCGC00169957-03, NCGC00387651-01, NCGC00179895-03, NCGC00108525-01, NCGC00071621-03, NCGC00131231-01, NCGC00246910-02, NCGC00108581-01, NCGC00107055-01, NCGC00263862-02, NCGC00072088-02, NCGC00357393-02, and NCGC00378623-01, or a prodrug, metabolite, or derivative of any of the foregoing, or a pharmaceutically acceptable salt of any of the foregoing; or a composition comprising at least one of the aforementioned compounds, and pharmaceutically acceptable carrier or diluent. In some embodiments, the cell is contacted with two or more of the aforementioned compounds, within the same formulation, or separate formulations.

In some embodiments, the flavivirus infection is Zika virus infection. In some embodiments, the flavivirus infection is dengue virus infection.

Optionally, the compound may be administered to a subject, or the cell contacted, with additional agents, such as other anti-flavivirus compounds, or other biologically active agents. For example, the additional agent may be one or more agents useful for treating or preventing flavivirus infection, or a symptom thereof. In some embodiments, the method further comprises administering an additional agent, wherein the anti-flavivirus compound and the additional agent are administered simultaneously, together within the same composition or in separate compositions. In other embodiments, the compound and the additional agent are administered consecutively in any order. Thus, one or more additional agents may be administered within the same formulation as the anti-flavivirus compound, or in a separate formulation before, during, and/or after administration of the anti-flavivirus compound.

Derivatives of any of the anti-flavivirus compounds can be synthesized by chemical transformations of the compounds' functional groups using standard chemical reactions. For example, these standard chemical reactions can include, but are not limited to: polar reactions under basic conditions, polar reactions under acidic conditions, pericyclic reactions, and free radical reactions. In another example, these standard chemical reactions can include, but are not limited to: addition reactions, substitution reactions, oxidation reactions, reduction reactions, elimination reactions, hydrolysis, acylation, amidations, etherification, and esterification. Alkane functional group transformations can include, but are not limited to: free radical chlorination (hv, $Cl_2$), free radical bromination (hv, $Br_2$), and allylic bromination (NBS). Alkene functional group transformations can include, but are not limited to: addition of HCl, addition of HBr, addition of HI, addition of $H_3O(+)$, chlorination ($Cl_2$) bromination ($Br_2$), iodination ($I_2$), chlorohydrin formation ($Cl_2/H_2O$), bromohydrin formation ($Br_2/H_2O$), ether formation ($H^+$/ROH), oxymercuration ($Hg(OAc)_2/H_2O$), oxymercuration, ($Hg(OAc)_2$/ROH), hydroboration, epoxidation ($RCO_3H$), dihydroxylation ($OsO_4$), dihydroxylation ($KMnO_4$), cyclopropanation, dichlorocyclopropanation, ozonolysis (reductive workup), ozonolysis (oxidative workup), oxidative cleavage ($KMnO_4$), hydrogenation, rearrangements (H shift), rearrangements (alkyl shift), free radical addition of HBr, and Sharpless epoxidation. Alkyne functional group transformations can include, but are not limited to: deprotonation (acetylide formation), $S_N2$ with alkyl halides, partial reduction (Lindlar), partial, reduction ($Na/NH_3$), hydroboration, oxymercuration, addition of HCl, HBr, or HI, addition of HCl, HBr, or HI, hydrogenation, ozonolysis, oxidative cleavage ($KMnO_4$), and halogenation ($Cl_2$, $Br_2$, $I_2$). The substitution reaction can include, but is not limited to: alcohol formation, nitrile formation, thiol formation, ether formation, thioether formation, azides, ester formation, acetylide addition, alkanes (Gilman reagents), ammonium salt formation, alkyl chloride formation, alkyl bromide formation, alkyl iodide formation, alkyl shift, and hydride shift. Elimination reactions can include, but are not limited to: alkenes from alkyl halides, alkenes from alcohols (strong acid), alkenes from alcohols ($POCl_3$), alkenes from alkyl halides, E1 with rearrangement (alkyl shift), Hofmann elimination, and alkyne formation via elimination E1 with rearrangement (hydride shift). Organometallic reactions can include, but are not limited to: Grignard formation (alkyl halides), Grignard formation (alkenyl halides), reaction of Grignards with acids, addition of Grignards to aldehydes, addition of Grignards to ketones, addition of Grignards to esters, reaction of Grignards with $CO_2$, addition of Grignards to nitriles, formation of organolithium reagents, formation of Gilman reagents, $S_N2$ with Gilman reagents, addition of Gilman reagents to enones, addition of Gilman to acyl halides, Heck reaction, Suzuki reaction, and Stille reaction. Reactions of epoxides can include, but are not limited to: epoxide opening (basic conditions), epoxide opening (acidic conditions), epoxide opening (diol formation), epoxide formation (from halohydrins), epoxide formation (from alkenes), and Sharpless epoxidation of alkenes. Reactions of alcohols and thiols can include, but are not limited to: deprotonation (alkoxide formation), protonation (onium ion formation), conversion to tosylates/mesylates, conversion to alkyl chlorides ($SOCl_2$), conversion to alkyl bromides ($PBr_3$), oxidation to aldehydes (PCC), oxidation to ketones (PCC+others), oxidation to carboxylic acid, ($H_2CrO_4$+others), protection as silyl ethers, thiol formation ($S_N2$), and thiol oxidation to disulfides. Reactions of dienes can include, but are not limited to: Diels-alder reaction, polymerization of dienes, reactions of aromatics (arenes), nitration ($HNO_3/H_2SO_4$), chlorination ($Cl_2$ plus catalyst), bromination ($Br_2$ plus catalyst), sulfonylation ($SO_3/H_2SO_4$), Friedel Crafts alkylation (R-X plus catalyst), Friedel Crafts acylation (RCOX plus catalyst), iodination ($I_2$/catalyst), Side chain oxidation ($KMnO_4$), reduction of nitro groups, reduction of aromatic ketones, Side chain bromination, nucleophilic aromatic substitution ($S_NAr$), and aryne formation ($S_NAr$ via arynes). Reactions of aldehydes and ketones can include, but are not limited to: hydrate formation ($H_2O$), cyanohydrin formation (CN), reduction of aldehydes ($NaBH_4$), reduction of aldehydes ($LiAlH_4$), reduction of ketones ($NaBH_4$), reduction of ketones ($LiAlH_4$), Grignard addition to aldehydes, Grignard addition to ketones, acetal formation ($ROH/H^+$), acetal hydrolysis ($H_3O^+$), imine, formation ($RNH_2$), Enamine formation ($R_2NH$), Wolff-Kishner: reduction to alkanes, Clemmensen, reduction to alkanes, oxidation to carboxylic acid ($H_2CrO_4$ or $KMnO_4$), keto-enol tautomerism, enolate formation, aldol addition reaction, alkylation of enolates, Wittig reaction (alkene formation), thioacetal formation, imine hydrolysis, oxidation to carboxylic acids (Tollens), haloform reaction, Baeyer-Villiger reaction, aldol condensation, Cannizarro reaction. Reactions of carboxylic acids can include, but are not limited to: deprotonation (carboxylate formation), formation via Grignard and $CO_2$, conversion to acid chloride ($SOCl_2$), reduction ($LiAlH_4$), Fischer esterification, and decarboxylation (of β-keto acids). Reactions of esters can include, but are not limited to: reduction to aldehydes (DIBAL-H), reduction to alcohols ($LiAlH_4$), hydrolysis to carboxylic acid (acidic), hydrolysis to carboxylic acid (basic), addition of Grignard reagents to esters, Claisen condensation, and transesterification (basic conditions). Reactions of acyl halides can include, but are not limited to: conversion to esters (ROH), conversion to carboxylic acids ($H_2O$), conversion to anhydrides ($RCO_2$), conversion to amides ($RNH_2$), conversion to ketones (Gilman reagents), and conversion to aldehydes ($LiAlH(OtBu)_3$). Reactions of α,β-unsaturated ketones (enones) can include, but are not limited to: Michael reaction (conjugate addition of enolates), conjugate addition of Gilman reagents, conjugate addition of other nucleophiles. Reactions of amines and amides can include, but are not limited to: dehydration of amides to nitriles ($P_2O_5$), Hofmann rearrangement, Gabriel synthesis of amines, reductive amination, formation of diazonium salts, reactions of diazonium salts, amide formation using DCC, amide formation from acid halides, and Curtius rearrangement. Reactions of nitriles can include, but are not limited to: addition of Grignard reagents to nitriles, reduction to amines ($LiAlH_4$), hydrolysis to carboxylic acids. Optionally, potential derivatives of compounds disclosed herein can be tested for the ability to inhibit virally-induced apoptosis and/or suppress viral replication, viral protein production using methods disclosed herein or using other methods known in the art (e.g., ATP cell viability assay).

In some embodiments of the methods, compositions, kits, and packaged dosage formulations of the invention, the Flavivirus infection is Zika virus, West Nile virus, dengue virus (e.g., type 1, 2, 3, or 4), tick-borne encephalitis virus, Japanese encephalitis virus, St. Louis encephalitis virus, or yellow fever virus. Other members of the genus can be found in Kuno G et al., *Journal of Virology,* 1998, "Phylogeny of the Genus Flavivirus," 72(1):73-83, which is incorporated herein by reference. In some embodiments, the Flavivirus is Zika virus. The Zika virus may be any origin or lineage (e.g., African, Asian, American, Brazilian). Examples of Zika virus strains include but are not limited to MR766 (1947 Uganda strain), FSS13025 (2010 Cambodian strain), PRVABC59 (2015 Puerto Rican strain), GZ01/2016 (2016 Chinese strain (ex Venezuela)), H/PF/2013 (2013 French Polynesian strain), IBH30656 (1968 Nigerian strain), Paraiba 2015 (2015 Brazilian strain), PLCal_ZV (2013 Canadian strain (ex Thailand)), SMGC-1 (2016 Chinese strain), SPH 2015 (2015 Brazilian strain), and SZ01 (2016 Chinese strain).

In each of the aforementioned methods, compositions, kits, and dosage formulations, additional agents (i.e., in addition to the one or more anti-flavivirus compounds) may be administered to the subject, contacted with the cell, or included in the compositions. In some embodiments, the additional agent is useful for the treatment or prevention of flavivirus infection, such as Zika virus infection or Dengue virus infection.

In some embodiments of the methods, compositions, kits, and packaged dosage formulations of the invention, two or more compounds useful for treating or preventing Zika virus, Dengue virus, or other flavivirus infection by distinct mechanisms of action from one another may be utilized. For example, compounds of the invention can inhibit or reduce Zika virus, Dengue virus, or other flavivirus replication, and thus represent one class of compounds of the invention. A combination of compounds may exhibit a synergistic effect in protecting cells from flavivirus-induced (e.g., Zika virus-induced or dengue-virus induced) cell death.

The methods of the invention may be used to treat an existing flavivirus infection in a subject, or the methods of the invention may be used prophylactically to prevent a flavivirus infection in a subject. As used herein, in this context, the term "prevent" or "prevention" is inclusive of delaying the onset of infection and/or one or more symptoms of infection, and precluding the occurrence or reoccurrence of infection and/or one or more symptoms of infection. Thus, in some embodiments, the subject has the flavivirus infection at the time the at least one compound is administered, and the at least one compound is administered as therapy.

In some embodiments, the methods further comprise, prior to administering the compound to the subject, identifying the subject as having the flavivirus infection. The identifying step may comprise assaying a biological sample (e.g., blood, saliva, or urine) obtained from the subject for the presence of flavivirus nucleic acids or flavivirus proteins (e.g., Zika virus nucleic acids or Zika virus proteins, or dengue virus nucleic acids or dengue virus proteins). In some embodiments, assaying includes the use of reverse transcriptase-polymerase chain reaction (RT-PCR), immunological assay (e.g., ELISA), or Plaque-reduction neutralization testing (PRNT).

One or more compounds of the invention (also referred to herein as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the subject. In some embodiments, at least one compound of the invention is administered orally, nasally, rectally, parenterally, subcutaneously, intramuscularly, or intravascularly (e.g., intravenously).

Another aspect of the invention concerns a packaged dosage formulation comprising at least one anti-flavivirus one compound in a pharmaceutically acceptable dosage in one or more packages, packets, or containers.

Another aspect of the invention concerns a kit comprising, in one or more containers, at least one anti-flavivirus compound.

In some embodiments, the kit comprises a combination of two or more anti-flavivirus compounds of the invention. In some embodiments, the kit further comprises an additional agent effective for the treatment or prevention of Flavivirus virus infection. In some embodiments, the kit further comprises an additional agent effective for the treatment of one or more symptoms of flavivirus infection.

Various techniques may be used to increase bioavailability of the anti-flavivirus compounds of the invention. Prodrugs employ various physical and chemical modifications to improve features of the active drug, and in some embodiments may be viewed as pharmacologically inactive prodrug functional groups that undergo a chemical transformation or enzymatic cleavage to liberate the active parent drug and produce the desired effect in the body. Utilizing a prodrug approach can yield benefits such as enhanced solubility, improved selective targeting of drugs to anatomical sites, protection from rapid metabolism and elimination, reduction toxic effects of an active drug on other parts of the body, and enhanced patient compliance.

Chemical reactions, reactants, and reagents that may be utilized to enhance solubility and make prodrugs of compounds are described in *March's Advanced Organic Chemistry*, 7$^{th}$ edition, 2013, Michael B. Smith, which is incorporated herein by reference in its entirety.

Compounds, and compositions comprising them, useful in the methods of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of at least one compound of the invention is combined with a suitable carrier or diluent in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers or diluents which are known to those skilled in the art. Examples of carriers or diluents for use with the subject peptides and polynucleotides include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of the compounds of the invention can also comprise suspension agents, protectants, lubricants, buffers, preservatives, and stabilizers. To provide for the administration of such dosages for the desired therapeutic treatment, pharmaceutical compositions of the invention will advantageously comprise between about 0.1% and 45%, and especially, 1 and 15% by weight of the total of one or more of the peptide or polynucleotide based on the weight of the total composition including carrier or diluent.

The anti-flavivirus compounds of the subject invention can also be administered utilizing liposome technology, slow release capsules, implantable pumps, and biodegradable containers. These delivery methods can, advantageously, provide a uniform dosage over an extended period of time.

The anti-flavivirus compounds of the invention can also be modified by the addition of chemical groups, such as PEG (polyethylene glycol). PEGylated compounds can exhibit extended half-lives in vivo in comparison to compounds that are not PEGylated when administered in vivo. Compounds can also be modified to improve cell membrane permeability. In one embodiment, cell membrane permeability can be improved by attaching a lipophilic moiety, such as a steroid, to the compound. In another embodiment, compounds of the invention can be coupled to a cell-penetrating peptide (CPP). CPPs are typically short peptides that are highly cationic and typically include several arginine and/or lysine amino acids. CPPs can be classified as hydrophilic, amphiphilic, or periodic sequence.

The subject invention also concerns a packaged dosage formulation comprising in one or more containers at least compound, and/or composition of the subject invention formulated in a pharmaceutically acceptable dosage. The package can contain discrete quantities of the dosage formulation, such as tablet, capsules, lozenge, and powders. The quantity of compound in a dosage formulation and that can be administered to a patient can vary from about 1 mg to about 5000 mg, or about 1 mg to about 2000 mg, or more typically about 1 mg to about 500 mg, or about 5 mg to about 250 mg, or about 10 mg to about 100 mg.

Optionally, the methods include, prior to administration of at least one compound of the invention, or re-administration of at least one compound of the invention, determining whether the subject has a Flavivirus infection (e.g., a Zika virus infection or dengue virus infection) or one or more symptoms consistent with a Flavivirus infection. The selectivity will vary with the detection method. Some methods can identify the infection only as a Flavivirus infection. Other methods can more selectively detect and identify the infection as a particular Flavivirus infection, such as a dengue virus infection, or specific type of dengue virus infection, for example.

The terms "selectively detect" or "selectively detecting" refer to the detection of Flavivirus, nucleic acids using oligonucleotides, e.g., primers, probes and/or capture oligonucleotides that are capable of detecting a particular Flavivirus virus nucleic acid, for example, by amplifying and/or binding to at least a portion of an RNA segment from a particular type of Flavivirus, but do not amplify and/or bind to sequences from other types of Flavivirus under appropriate hybridization conditions. For example, in the context of DENV, the terms "selectively detect" or "selectively detecting" refer to the detection of dengue virus nucleic acids using oligonucleotides, e.g., primers, probes and/or capture oligonucleotides that are capable of detecting a particular dengue virus nucleic acid, for example, by amplifying and/or binding to at least a portion of an RNA segment from a particular type of dengue virus, such as a particular dengue virus serotype (e.g., DENV-1, DENV-2, DENV-3, or DENV-4), but do not amplify and/or bind to sequences from other types of dengue viruses under appropriate hybridization conditions.

In the case of Zika virus, during the first week after onset of symptoms, viral RNA can often be identified in serum; thus, Zika virus disease can be diagnosed by performing reverse transcriptase-polymerase chain reaction (RT-PCR) on serum. Urine and saliva samples may also be used for detection of Zika virus (Gourinat A-C et al. (2015) *Emerg Infect Dis*, vol. 21, no. 1, pp. 84-86; and Musso D et al. (2015) *J Clin Virol*, vol. 68, pp. 53-55).

Virus-specific IgM and neutralizing antibodies typically develop toward the end of the first week of illness; cross-reaction with related flaviviruses (e.g., dengue and yellow fever viruses) is common and may be difficult to discern. Plaque-reduction neutralization testing (PRNT) can be performed to measure virus-specific neutralizing antibodies and discriminate between cross-reacting antibodies in primary flavivirus infections.

Conventional laboratory techniques/tools are available for the diagnosis of DENV. Confirmation of DENV can be made through virus isolation, genome amplification, as well, as antigen and antibody detection via serology. Selection of a suitable test can be dependent on a variety of factors such as viremia period and infection status (primary or secondary). Examples of tests include viral culture using biological samples such as plasma, serum peripheral blood, cerebrospinal fluid, pleural fluid, and immune system tissues, such as the liver, spleen, and lymph node; nucleic acid amplification (e.g., by RT-PCR); and serological diagnosis such as hemagglutination inhibition (HI) assay, detection of dengue-specific IgM antibody (e.g., by ELISA or rapid test), detection of dengue-specific IgG antibody, and detection of dengue NS1 (e.g., by ELISA or rapid test). Methods and tools for detection of DENV and diagnosis of dengue infection can be found, for example, in Nguyen et al. (*Int. J. Mol. Sci.*, 2019, 20:3464), Pang et al. (*J. Clin. Microbiol.*, 2017, 55:3339-3349), Parkash et al. (*Viruses*, 2015, 7:5410-5427), Muller et al. (*J. Infect. Dis.*, 2017, 215(Suppl 2):S89-S95), Fatima et al. (*Pak. J. Pharm. Sci.*, 2015, 28:271-280), Huhtamo et al. (*J. Clin. Virol.*, 2010, 47:49-53), which are each incorporated herein by reference in their entirety.

In the case of Zika virus, some infected individuals will not know they have the disease because they will not have symptoms. The most common symptoms of Zika virus infection are fever, maculo-papular rash (often spreading from face to body), joint pain, retro-orbital pain, or conjunctivitis (red eyes). Other common symptoms include general non-specific such as myalgia, asthenia, and headache. The incubation period (the time from exposure to symptoms) for Zika virus disease is not known, but is likely to be a few days to a week. The illness is usually mild with symptoms lasting for several days to a week after being bitten by an infected mosquito. The Zika virus usually remains in the blood of an infected person for approximately a week but it can be found longer in some individuals.

In the case of dengue virus (DENV), dengue fever causes a spectrum of presentations ranging from mild self-limiting illness to severe disease. Clinical symptoms of DENV may include one or more of the following: flu-like symptoms, rash, diarrhea, muscle/joint pain, neurological manifestation, bleeding tendency, and thrombocytopenia. Subjects presenting with all four criteria of fever, hemmorhagic diathesis, thrombocytopenia, and evidence of plasma leakage will typically be classified as having DHF, or DSS if they present with symptoms of shock (based on 1997 WHO dengue classification). The severity classification now includes dengue, dengue with warning signs, and severe dengue. The subject may have any of these before or after administration of the at least one compound.

Treatment methods optionally include steps of advising that the subject get plenty of rest and drink fluids for hydration and administration of agents that alleviate symptoms of Flavivirus infection (e.g., dengue virus infection or Zika virus infection), such as those that reduce fever and pain (e.g., acetaminophen and/or paracetamol). The methods may include administration of the fluids to the subject for hydration.

The subject may be any age or gender. In some embodiments, the subject is male. In some embodiments, the subject is female. In some embodiments, the subject is a post-pubescent female. In some embodiments, the subject is a post-pubescent, pre-menopausal female. In some embodiments, the subject is a non-pregnant female. In some embodiments, the subject is a pregnant female. In some embodiments, the subject has Guillain-Barré syndrome or another condition that is associated with ZIKV infection.

In some embodiments, the Flavivirus is DENV, the subject has mild or severe dengue fever at the time of administration, and at least one compound is administered to the subject as therapy. In some embodiments, the Flavivirus is DENV, at least one compound is administered prior to infection, and administration prevents or delays onset of dengue fever (mild or severe dengue fever). In some embodiments, the at least one compound is administered to the subject as therapy for dengue hemorrhagic fever (DHF) or dengue shock syndrome (DSS), or to prevent or delay the onset of DHF or DSS.

The invention further provides kits, including at least one compound of the invention and pharmaceutical formulations, packaged into suitable packaging material, optionally in combination with instructions for using the kit components, e.g., instructions for performing a method of the invention. In one embodiment, a kit includes an amount of at least one compound of the invention, and instructions for administering at least one compound of the invention to a subject in need of treatment on a label or packaging insert. In further embodiments, a kit includes an article of manufacture, for delivering at least one compound of the invention into a subject locally, regionally or systemically, for example.

As used herein, the term "packaging material" refers to a physical structure housing the components of the kit. The packaging material can maintain the components in a sterile state, and can be made of material commonly used for such purposes (e.g., paper, corrugated fiber, glass, plastic, foil, ampules, etc.). The label or packaging insert can include appropriate printed and/or digital instructions, for example, for practicing a method of the invention, e.g., treating a Flavivirus infection (e.g., Zika virus infection or dengue virus infection), an assay for identifying a subject having a Flavivirus infection (e.g., Zika virus infection or dengue virus infection), etc. Thus, in additional embodiments, a kit includes a label or packaging insert including instructions for practicing a method of the invention in solution, in vitro, in vivo, or ex vivo.

Instructions can therefore include instructions for practicing any of the methods of the invention described herein. For example, pharmaceutical compositions can be included in a container, pack, or dispenser together with instructions for administration to a subject to treat a flavivirus infection (e.g., Zika virus infection or dengue virus infection). Instructions may additionally include indications of a satisfactory clinical endpoint or any adverse symptoms that may occur, storage information, expiration date, or any information required by regulatory agencies such as the Food and Drug Administration or European Medicines Agency for use in a human subject.

The instructions may be digital or on "printed matter," e.g., on paper or cardboard within the kit, on a label affixed to the kit or packaging material, or attached to a vial or tube containing a component of the kit. Instructions may comprise voice or video tape and additionally be included on a computer readable medium, such as a disk (diskette or hard disk), optical CD such as CD- or DVD-ROM/RAM, magnetic tape, electrical storage media such as RAM and ROM and hybrids of these such as magnetic/optical storage media.

Kits can additionally include a buffering agent, a preservative, or an agent for stabilizing at least one compound of the invention. The kit can also include components for assaying for the presence of Zika virus, dengue virus, or other Flavivirus, e.g., an antibody or antibody fragment specific for a Zika virus, dengue virus, or other Flavivirus antigen, one or more primers specific for Zika virus, dengue virus, or other Flavivirus nucleic acids, a control sample or a standard. Each component of the kit can be enclosed within an individual container or in a mixture and all of the various containers can be within single or multiple packages.

Kits can include packaging material that is compartmentalized to receive one or more containers such as vials, tubes, and the like, each of the container(s) including one of the separate elements to be used in a method described herein. Packaging materials for use in packaging pharmaceutical products include, by way of example only U.S. Pat. Nos. 5,323,907, 5,052,558 and 5,033,252. Examples of pharmaceutical packaging materials include, but are not limited to, blister packs, bottles, tubes, pumps, bags, vials, light-tight sealed containers, syringes, bottles, and any packaging material suitable for a selected formulation and intended mode of administration and treatment.

A kit may include one or more additional containers, each with one or more of various materials desirable from a commercial and user standpoint for use of the compounds for treating or preventing Zika virus, dengue virus, or other Flavivirus infection. Non-limiting examples of such materials include, but not limited to, buffers, diluents, carrier, package, container, vial and/or tube labels listing contents and/or instructions for use, and package inserts with instructions for use.

A label can be on or associated with a container containing a compound of the invention. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In some embodiments of the kit, the compound(s) of the invention can be presented in a pack or dispenser device which can contain one or more unit dosage forms containing a compound disclosed herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

Additional anti-flavivirus compounds can be identified by determining whether the candidate compounds reduce virally-induced apoptosis and/or suppress viral replication.

Definitions

The terms "compounds of the invention", "compounds of the present invention", "anti-flavivirus compound of the invention", or "anti-flavivirus compound of the invention" (unless specifically identified otherwise), and grammatical variations thereof, refer to the compounds and classes of compounds disclosed herein, such as at least one compound selected from the group consisting of: NCGC00102779-01, NCGC00113159-01, NCGC00104879-01, NCGC00025125-18, NCGC00018238-09, NCGC00112058-01, NCGC00169957-03, NCGC00387651-01, NCGC00179895-03, NCGC00108525-01, NCGC00071621-03, NCGC00131231-01, NCGC00246910-02, NCGC00108581-01, NCGC00107055-01, NCGC00263862-02, NCGC00072088-02, NCGC00357393-02, and NCGC00378623-01 (the chemical structures of which are shown in Table 1), or a prodrug, metabolite, or derivative of any of the foregoing, or a pharmaceutically acceptable salt of any of the foregoing. Compounds of the invention include stereoisomers (including diastereoisomers and enantiomers), rotamers, tautomers and isotopically labeled compounds (including deuterium substitutions), as well as inherently formed moieties (e.g., polymorphs, solvates and/or hydrates) of the aforementioned compounds. For purposes of this invention, solvates and hydrates are generally considered compositions.

The term "a," "an," "the" and similar terms used in the context of the present invention (especially in the context of the claims) are to be construed to cover both the singular and plural unless otherwise indicated herein or clearly contradicted by the context. Thus, for example, reference "a cell" or "a compound" should be construed to cover both a singular cell or singular compound and a plurality of cells and a plurality of compounds unless indicated otherwise or clearly contradicted by the context.

The term "agent" refers to all materials that may be used as or in a pharmaceutical composition, or that may be a compound such as small synthetic or naturally derived organic compounds, nucleic acids, polypeptides, antibodies, fragments, isoforms, variants, or other materials that may be used independently for such purposes.

The term "small molecule" refers to a composition that has a molecular weight of less than about 3 kilodaltons (kDa), less than about 1 kDa, or less than about 1 kDa. Small molecules may be nucleic acids, peptides, polypeptides, peptidomimetics, carbohydrates, lipids, or other organic (carbon-containing) or inorganic molecules. A "small organic molecule" is an organic compound (or organic compound complexed with an inorganic compound (e.g., metal), that has a molecular weight of less than about 3 kDa, less than about 1.5 kDa, or less than about 1 kDa.

The term "isolated," when used as a modifier of a composition of matter, such as a compound, means that the compositions are made by the hand of man or are separated from their naturally occurring in vivo environment. Generally, compositions so separated are substantially free of one or more materials with which they normally associate with in nature, for example, one or more protein, nucleic acid, lipid, carbohydrate, cell membrane. A "substantially pure" molecule can be combined with one or more other molecules. Thus, the term "substantially pure" does not exclude combinations of compositions. Substantial purity can be at least about 60% or more of the molecule by mass. Purity can also be about 70% or 80% or more, and can be greater, for example, 90% or more. Purity can be determined by any appropriate method, including, for example, UV spectroscopy, chromatography (e.g., HPLC, gas phase), gel electrophoresis (e.g., silver or coomassie staining) and sequence analysis (for nucleic acid and peptide). The compounds of the invention may be in isolated or substantially pure form.

The present invention includes derivatives of identified compounds, also referred to herein as pharmaceutically active derivatives. "Pharmaceutically active derivative" refers to any compound that upon administration to the subject or cell, is capable of providing directly or indirectly, the activity disclosed herein. The term "indirectly" also encompasses prodrugs which may be converted to the active form of the drug via endogenous enzymes or metabolism. The prodrug is a derivative of the compounds according to the invention and presenting flavivirus (e.g., Zika virus or dengue virus) inhibitory activity and/or protective activity against effects of flavivirus (e.g., Zika virus or dengue virus) that has a chemically or metabolically decomposable group, and a compound that may be converted into a pharmaceutically active compound according to the invention in vivo by solvolysis under physiological conditions. The prodrug is converted into a compound according to the present invention by a reaction with an enzyme, gastric acid or the like under a physiological condition in the living body, e.g., by oxidation, reduction, hydrolysis or the like, each of which is carried out enzymatically. These compounds can be produced from compounds of the invention according to well-known methods. The term "indirectly" also encompasses metabolites of compounds according to the invention. Chemical reactions, reactants, and reagents useful for making derivatives can be found, for example, in *March's Advanced Organic Chemistry,* 7$^{th}$ edition, 2013, Michael B. Smith, which is incorporated herein by reference in its entirety.

The term "metabolite" refers to all molecules derived from any of the compounds according to the invention in a cell or organism, preferably mammal. Pharmaceutically active metabolites of the compounds of the invention may be administered to a subject or contacted with a cell in vitro or in vivo.

The term "prodrug" refers to a chemical compound that can be converted by the body (i.e., biotransformed) to another chemical compound that has pharmacological activity. The prodrug may itself have pharmacological activity before conversion, or be inactive before conversion and activated upon conversion. Active prodrugs or inactive prodrugs of compounds of the invention may be administered to a subject or contacted with a cell in vitro or in vivo. Instead of administering a drug directly, a prodrug may be used instead to improve how a drug is absorbed, distributed, metabolized, and excreted (ADME). For example, a prodrug may be used to improve bioavailability when a drug itself is poorly absorbed from the gastrointestinal tract, or to improve how selectively the drug interacts with cells or processes that are not its intended target, which can reduce adverse or unintended effects of a drug. Major types of prodrugs include, but are not limited to, type I prodrugs, which are biotransformed inside cells (intracellularly), and type II prodrugs, which are biotransformed outside cells (extracellularly), such as in digestive fluids or in the body's circulatory system. These types can be further categorized into subtypes based on factors such as whether the intracellular bioactivation location is also a site of therapeutic action, or whether or not bioactivation occurs in the gastrointestinal fluids or in the circulation system (Wu, Kuei-Meng, "A New Classification of Prodrugs: Regulatory Perspectives, *Pharmaceuticals,* 2009, 2(3):77-81, which is incorporated by reference herein in its entirety).

Pharmaceutical formulations include "pharmaceutically acceptable" and "physiologically acceptable" carriers, diluents or excipients. As used herein the terms "pharmaceutically acceptable" and "physiologically acceptable" carriers, diluents, or excipients include solvents (aqueous or non-aqueous), solutions, emulsions, dispersion media, coatings, isotonic and absorption promoting or delaying agents, compatible with pharmaceutical administration. Such formulations can be contained in a liquid; emulsion, suspension, syrup or elixir, or solid form; tablet (coated or uncoated), capsule (hard or soft), powder, granule, crystal, or micro-bead. Supplementary compounds (e.g., preservatives, antibacterial, antiviral and antifungal agents) can also be incorporated into the compositions. The phrase "pharmaceutically acceptable" indicates that the substance or composition must be compatible chemically and/or toxicologically, with the other ingredients comprising a formulation, and/or the mammal and/or cells being treated therewith. Examples of pharmaceutically acceptable carriers include but are not limited to saline, buffered saline, isotonic saline, Ringer's solution, dextrose, sterile water, deionized water, glycerol, ethanol, 5% dextrose in water, propylene glycol, and combinations of two or more of the foregoing.

The phrase "effective amount", in the context of a subject, means an amount of at least one compound of the invention that (i) treats or prevents the particular disease, condition, or disorder (e.g., Zika, dengue, or other flavivirus infection) in a subject, (ii) attenuates, ameliorates, or eliminates one or more symptoms of the particular disease, condition, or disorder (e.g., Zika, dengue, or other flavivirus infection) in a subject, or (iii) prevents or delays the onset of one or more symptoms of the particular disease, condition, or disorder described herein (e.g., Zika, dengue or other flavivirus infection) in a subject.

The phrase "effective amount", in the context of a cell in vitro or in vivo, means an amount of at least one compound of the invention that (i) treats or prevents the particular disease, condition, or disorder (e.g., Zika, dengue, or other flavivirus infection) in a cell, (ii) attenuates, ameliorates, or eliminates one or more effects of the particular disease, condition, or disorder (e.g., Zika, dengue, or other flavivirus infection) in a cell, or (iii) prevents or delays the onset of one or more effects of the particular disease, condition, or disorder described herein (e.g., Zika, dengue, or other flavivirus infection) in a subject.

As used herein, a subject is "in need of" a treatment if such human or non-human animal subject would benefit biologically, medically or in quality of life from such treatment (preferably, a human). In some embodiments, the subject has a flavivirus infection and is in need of therapy. In other embodiments, the subject does not have a flavivirus infection and is in need of prophylaxis. In some embodiments, the subject in need of prophylaxis is at risk of becoming infected with the flavivirus. In some embodiments, the subject is at increased risk of becoming infected with the flavivirus relative to others in the population. In some embodiments, the subject is suspected to have a flavivirus infection.

As used herein, the term "inhibit", "inhibition" or "inhibiting" refers to the reduction or suppression of a given condition, symptom, or disorder, or disease (e.g., Zika virus, dengue virus, or other flavivirus infection, or Zika viral, dengue viral, or other flavivirus load or titer), or a significant decrease in the baseline activity of a biological activity or process (inhibits or suppresses Zika, dengue, or other flavivirus infection, or inhibits or suppresses Zika, dengue, or other flavivirus replication, or inhibits or suppresses Zika-induced or other flavivirus-induced neural cell death.

As used herein, the terms "subject", "patient", and "individual" refer to a human or non-human animal. Typically, the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human. The subject may be any age or gender. For example, in some embodiments, the subject is a female. In some embodiments, the subject is a post-pubescent female or a post-pubescent female. In some embodiments, the subject is a pregnant female; in other embodiments, the subject is a non-pregnant female.

In some embodiments, the subject has been exposed to the Flavivirus and/or has the Flavivirus infection at the time the at least one compound is administered. In some embodiments, the Flavivirus is DENV, the subject has mild or severe dengue fever at the time of administration, and administration is provided to the subject as therapy. In some embodiments, the Flavivirus is DENV, and the at least one compound is administered prior to infection, and administration prevents or delays onset of dengue fever (mild or severe dengue fever). In some embodiments, the at least one compound is administered to the subject as therapy for dengue hemorrhagic fever (DHF) or dengue shock syndrome (DSS), or to prevent or delay the onset of DHF or DSS.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the subject. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to prophylaxis (preventing or delaying the onset or development or progression of the disease or disorder).

As used herein, the term "administration" is intended to include, but is not limited to, the following delivery methods: topical, oral, parenteral, subcutaneous, transdermal, transbuccal, intravascular (e.g., intravenous or intra-arterial), intramuscular, subcutaneous, intranasal, and intra-ocular administration. Administration can be local at a particular anatomical site, such as a site of infection, or systemic. Administration can be by any route effective to treat, prevent, or delay onset of the Flavivirus infection in the subject.

As used herein, the term "contacting" in the context of contacting a cell with at least one compound of the invention in vitro or in vivo means bringing at least one compound into contact with the cell, or vice-versa, or any other manner of causing the compound and the cell to come into contact. In those embodiments of the method for inhibiting flavivirus infection in human or non-human animal cells in vitro or in vivo, when a cell is contacted with a compound in vivo, the compound is administered to a subject, and the administration may occur by any route (e.g., topical, oral, parenteral, subcutaneous, transdermal, transbuccal, intravascular (e.g., intravenous or intra-arterial), intramuscular, subcutaneous, intranasal, and intra-ocular administration).

The compounds of the present invention can be formulated into pharmaceutically-acceptable salt forms. Pharmaceutically-acceptable salts of the compounds of the invention can be prepared using conventional techniques. "Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts described herein are pharmaceutically acceptable acid addition salts and pharmaceutically acceptable base addition salts. "Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bi sulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., *supra*.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Antiviral Activity of Compounds Against Zika Virus and Dengue Virus

The inventors have identified 19 compounds with antiviral activity against Zika virus and/or dengue virus. These compounds are: NCGC00102779-01, NCGC00113159-01, NCGC00104879-01, NCGC00025125-18, NCGC00018238-09, NCGC00112058-01, NCGC00169957-03, NCGC00387651-01, NCGC00179895-03, NCGC00108525-01, NCGC00071621-03, NCGC00131231-01, NCGC00246910-02, NCGC00108581-01, NCGC00107055-01, NCGC00263862-02, NCGC00072088-02, NCGC00357393-02, and NCGC00378623-01. The compounds were initially identified via a computational model.

These 19 compounds were further validated for antiviral activity by a Zika viral production assay and also by analyzing protein production via Western blot in dengue virus-infected cells. Human glioblastoma cells were treated with individual compounds for 1 hour prior to infection with Zika virus or dengue virus for 24 hours. After 24 hours, cellular lysate was harvested for Western blot analysis of viral protein levels (DENV infection), or supernatant collected and used to infect Vero cells in an infectious viral titer assay (ZIKV infection). The results are shown in Table 2, below.

TABLE 2

| Sample ID and IUPAC Name | Anti-DENV Activity at 1 uM (SNB-19 cells) | Anti-DENV Activity at 10 uM (SNB-19 cells) | Anti-ZIKV activity IC50 |
|---|---|---|---|
| 1 NCGC00179895-03 ((2S,2'R,3'R,4'S,5'S,5a'R,9a'R)-4'-acetoxy-3'-hydroxy-5',8'-dimethyl-2',3',4',5',7',9a'-hexahydrospiro[oxirane-2,10'[2,5]methanobenzo[b]oxepin]-5a'(6'H)-yl)methyl acetate | Yes | Yes | 3.49E−09 |
| 2 NCGC00387651-01 (2S,2'R,3'R,4'S,5'S,5a'R,7'S,9a'R)-4'-acetoxy-5a'-(acetoxymethyl)-3'-hydroxy-5',8'-dimethyl-2',3',4',5',5a',6',7',9a'-octahydrospiro[oxirane-2,10'-[2,5]methanobenzo[b]oxepin]-7'-yl 3-methylbutanoate | Yes | Yes | 4.38E−09 |
| 3 NCGC00169957-03 3-(sec-butyl)-16-isobutyl-6-isopropyl-5,8,9-trimethyldodecahydropyrrolo[1,2-d][1]oxa[4,7,10,13,16]pentaazacyclononadecine-1,4,7,10,14,17(11H,16H)-hexaone | No | Yes | 6.13E−07 |
| 4 NCGC00108525-01 ethyl 4-(3-(4-methoxyphenyl)-6-oxo-4-(p-tolyl)-4,6-dihydropyrrolo[3,4-c]pyrazol-5(1H)-yl)benzoate | No | Yes | 1.37E−07 |
| 5 NCGC00246910-02 7-(3,4-dihydroxy-5-(hydroxymethyl)tetrahydrofuran-2-yl)-1,7-dihydro-4H-pyrrolo[2,3-d]pyrimidin-4-one | No | Yes | 2.70E−07 |
| 6 NCGC00072088-02 N-(pyridin-3-yl)thiophene-2-carboxamide | No | Yes | 2.35E−06 |

TABLE 2-continued

| Sample ID and IUPAC Name | Anti-DENV Activity at 1 uM (SNB-19 cells) | Anti-DENV Activity at 10 uM (SNB-19 cells) | Anti-ZIKV activity IC50 |
|---|---|---|---|
| 7 NCGC00108581-01<br>ethyl 4-(3-(furan-2-yl)-6-oxo-4-(p-tolyl)-2,6-dihydropyrrolo[3,4-c]pyrazol-5(4H)-yl)benzoate | No | Yes | 2.42E−06 |
| 8 NCGC00357393-02<br>(2S,3R,4S,4aR)-2,3,4,7-tetrahydroxy-3,4,4a,5-tetrahydro-[1,3]dioxolo[4,5-j]phenanthridin-6(2H)-one | Yes | Yes | 6.74E−10 |
| 9 NCGC00102779-01<br>5-(4-ethoxyphenyl)-4-(3-fluorophenyl)-3-thiophen-2-yl-2,4-dihydropyrrolo[3,4-c]pyrazol-6-one | No | No | 9.24E−06 |
| 10 NCGC00113159-01<br>methyl 4-[[5-methyl-2-(4-methylphenyl)-1,3-oxazol-4-yl]methyl]furo[3,2-b]pyrrole-5-carboxylate | No | No | >30 μM |
| 11 NCGC00104879-01<br>N-[(2-chlorophenyl)methyl]-3-(2-methoxyethyl)-2,4-dioxo-1H-quinazoline-7-carboxamide | No | No | >30 μM |
| 12 NCGC00025125-18<br>N-[(7S)-1,2,3,10-tetramethoxy-9-oxo-6,7-dihydro-5H-benzo[a]heptalen-7-yl]acetamide | No | No | 7.09E−10 |
| 13 NCGC00018238-09<br>methyl N-(6-propoxy-1H-benzimidazol-2-yl)carbamate | No | No | 2.33E−10 |
| 14 NCGC00112058-01<br>N-[(2-chlorophenypmethyl]-6,7,10-trimethylbenzo[b][1,4]benzothiazepine-3-carboxamide | No | No | >30 μM |
| 15 NCGC00071621-03<br>4-[3-(2-methoxyphenyl)-[1,2,4]triazolo[3,4-b][1,3,4]thiadiazol-6-yl]-N,N-dimethylaniline | No | No | >30 μM |
| 16 NCGC00131231-01<br>4-tert-butyl-N-[1-(thiophene-2-carbonyl)-3,4-dihydro-2H-quinolin-6-yl]benzamide | No | No | 7.60E−06 |
| 17 NCGC00107055-01<br>9-(3-bromo-4,5-dimethoxyphenyl)-3,6,8,9-tetrahydro-2H-[1,4]dioxino[2,3-g]quinolin-7-one | No | No | 2.85E−08 |
| 18 NCGC00263862-02<br>5-fluoro-1-((4R,5R)-4-hydroxy-5-(hydroxymethyl)tetrahydrofuran-2-yl)pyrimidine-2,4(1H,3H)-dione | No | No | 1.65E−08 |
| 19 NCGC00378623-01<br>(S)-2-((S)-2-(dimethylamino)-3-methylbutanamido)-N-((3R,4S,5S)-3-methoxy-1-((S)-2-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N,3-dimethylbutanamide | No | No | 1.78E−15 |

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

Exemplified Embodiments

Examples of claimed embodiments of the invention include, but are not limited to:

Embodiment 1. A method for treating or preventing Flavivirus infection in a human or non-human animal subject, said method comprising administering an effective amount of at least one compound to a subject in need thereof, wherein the compound is selected from the group consisting of NCGC00102779-01, NCGC00113159-01, NCGC00104879-01, NCGC00018238-09, NCGC00169957-03, NCGC00179895-03, NCGC00071621-03, NCGC00246910-02, NCGC00107055-01, NCGC00072088-02, NCGC00025125-18, NCGC00112058-01, NCGC00387651-01, NCGC00108525-01, NCGC00131231-01, NCGC00108581-01, NCGC00263862-02, NCGC00357393-02, and NCGC00378623-01, or a prodrug, metabolite, or derivative of any of the foregoing, or a pharmaceutically acceptable salt of any of the foregoing.

Embodiment 2. The method of embodiment 1, wherein the Flavivirus infection is Zika virus infection.

Embodiment 3. The method of embodiment 1, wherein the Flavivirus infection is dengue virus infection.

Embodiment 4. The method of any one of embodiments 1 to 3, wherein the subject has the Flavivirus infection at the time of said administering, and the at least one compound is administered as therapy.

Embodiment 5. The method of embodiment 4, further comprising, prior to said administering, identifying the subject as having the Flavivirus infection.

Embodiment 6. The method of embodiment 5, wherein said identifying comprises assaying a biological sample obtained from the subject for the presence of Flavivirus nucleic acids or Flavivirus proteins.

Embodiment 7. The method of embodiment 6, wherein said assaying comprises use of reverse transcriptase-polymerase chain reaction (RT-PCR), immunological assay, or Plaque-reduction neutralization testing (PRNT).

Embodiment 8. The method of embodiment 1, wherein the subject does not have the Flavivirus infection at the time of said administering, and the at least one compound is administered as prophylaxis.

Embodiment 9. The method of any preceding embodiment, wherein the at least one compound is administered orally, nasally, rectally, parenterally, subcutaneously, intramuscularly, or intravascularly.

Embodiment 10. The method of embodiment 1, further comprising administering an additional agent for treating or preventing Flavivirus infection, or a symptom thereof, in the same formulation as the at least one compound, or in a separate formulation before, during, or after administration of the at least one compound.

Embodiment 11. The method of any preceding embodiment, wherein two or more compounds selected from the group consisting of NCGC00102779-01, NCGC00113159-01, NCGC00104879-01, NCGC00025125-18, NCGC00018238-09, NCGC00112058-01, NCGC00169957-03, NCGC00387651-01, NCGC00179895-03, NCGC00108525-01, NCGC00071621-03, NCGC00131231-01, NCGC00246910-02, NCGC00108581-01, NCGC00107055-01, NCGC00263862-02, NCGC00072088-02, NCGC00357393-02, and NCGC00378623-01, or a prodrug, metabolite, or derivative of any of the foregoing, or a pharmaceutically acceptable salt of any of the foregoing, are administered to the subject, in the same composition or in different compositions.

Embodiment 12. The method of any preceding embodiment, wherein the at least one compound is administered to the subject in a pharmaceutical composition comprising the at least one compound and a pharmaceutically acceptable carrier or diluent.

Embodiment 13. A method for inhibiting flavivirus infection in human or non-human animal cells in vitro or in vivo, said method comprising contacting an effective amount of at least one compound to a human or non-human animal cell in vitro or in vivo before or after exposure of the cell to Flavivirus, wherein the at least one compound is selected from the group consisting of NCGC00102779-01, NCGC00113159-01, NCGC00104879-01, NCGC00025125-18, NCGC00018238-09, NCGC00112058-01, NCGC00169957-03, NCGC00387651-01, NCGC00179895-03, NCGC00108525-01, NCGC00071621-03, NCGC00131231-01, NCGC00246910-02, NCGC00108581-01, NCGC00107055-01, NCGC00263862-02, NCGC00072088-02, NCGC00357393-02, and NCGC00378623-01, or a prodrug, metabolite, or derivative of any of the foregoing, or a pharmaceutically acceptable salt of any of the foregoing.

Embodiment 14. The method of embodiment 13, wherein the Flavivirus infection is Zika virus infection.

Embodiment 15. The method of embodiment 13, wherein the Flavivirus infection is dengue virus infection.

Embodiment 16. A packaged dosage formulation comprising at least one compound, wherein the at least one compound is in a pharmaceutically acceptable dosage in one or more packages, packets, or containers, and wherein the at least one compound is selected from the group consisting of NCGC00102779-01, NCGC00113159-01, NCGC00104879-01, NCGC00025125-18, NCGC00018238-09, NCGC00112058-01, NCGC00169957-03, NCGC00387651-01, NCGC00179895-03, NCGC00108525-01, NCGC00071621-03, NCGC00131231-01, NCGC00246910-02, NCGC00108581-01, NCGC00107055-01, NCGC00263862-02, NCGC00072088-02, NCGC00357393-02, and NCGC00378623-01, or a prodrug, metabolite, or derivative of any of the foregoing, or a pharmaceutically acceptable salt of any of the foregoing.

Embodiment 17. The packaged dosage formulation of embodiment 16, comprising two or more of the compounds selected from the group consisting of NCGC00102779-01, NCGC00113159-01, NCGC00104879-01, NCGC00025125-18, NCGC00018238-09, NCGC00112058-01, NCGC00169957-03, NCGC00387651-01, NCGC00179895-03, NCGC00108525-01, NCGC00071621-03, NCGC00131231-01, NCGC00246910-02, NCGC00108581-01, NCGC00107055-01, NCGC00263862-02, NCGC00072088-02, NCGC00357393-02, and NCGC00378623-01, or a prodrug, metabolite, or derivative of any of the foregoing, or a pharmaceutically acceptable salt of any of the foregoing.

Embodiment 18. A kit comprising, in one or more containers, at least one compound; and packaging material, wherein the at least one compound is selected from the group consisting of NCGC00102779-01, NCGC00113159-01, NCGC00104879-01, NCGC00025125-18, NCGC00018238-09, NCGC00112058-01, NCGC00169957-03, NCGC00387651-01, NCGC00179895-03, NCGC00108525-01, NCGC00071621-03, NCGC00131231-01, NCGC00246910-02, NCGC00108581-01, NCGC00107055-01, NCGC00263862-02, NCGC00072088-02, NCGC00357393-02, and NCGC00378623-01, or a prodrug, metabolite, or derivative of any of the foregoing, or a pharmaceutically acceptable salt of any of the foregoing.

Embodiment 19. The kit of embodiment 18, further comprising instructions for using the at least one compound or composition (e.g., for treating or preventing a flavivirus infection, such as Zika virus infection or dengue virus infection).

Embodiment 20. The kit of embodiment 18 or 19, comprising two or more of the compounds selected from the group consisting of NCGC00102779-01, NCGC00113159-01, NCGC00104879-01, NCGC00025125-18, NCGC00018238-09, NCGC00112058-01, NCGC00169957-03, NCGC00387651-01, NCGC00179895-03, NCGC00108525-01, NCGC00071621-03, NCGC00131231-01, NCGC00246910-02, NCGC00108581-01, NCGC00107055-01, NCGC00263862-02, NCGC00072088-02, NCGC00357393-02, and NCGC00378623-01, or a prodrug, metabolite, or derivative of any of the foregoing, or a pharmaceutically acceptable salt of any of the foregoing.

REFERENCES

1. Dick, G. W., Kitchen, S. F. & Haddow, A. J. Zika virus. I. Isolations and serological specificity. *Trans R Soc Trop Med Hyg* 46, 509-520 (1952).

2. Duffy, M. R., et al. Zika virus outbreak on Yap Island, Federated States of Micronesia. *N Engl J Med* 360, 2536-2543 (2009).
3. Cao-Lormeau, V. M., et al. Zika virus, French polynesia, South pacific, 2013. *Emerg Infect Dis* 20, 1085-1086 (2014).
4. Musso, D. Zika Virus Transmission from French Polynesia to Brazil. *Emerg Infect Dis* 21, 1887 (2015).
5. Heymann, D. L., et al. Zika virus and microcephaly: why is this situation a PHEIC? *Lancet* 387, 719-721 (2016).
6. Mlakar, J., et al. Zika Virus Associated with Microcephaly. *N Engl J Med* 374, 951-958 (2016).
7. Rasmussen, S. A., Jamieson, D. J., Honein, M. A. & Petersen, L. R. Zika Virus and Birth Defects—Reviewing the Evidence for Causality. *N Engl J Med* 374, 1981-1987 (2016).
8. Cao-Lormeau, V. M., et al. Guillain-Barre Syndrome outbreak associated with Zika virus infection in French Polynesia: a case-control study. *Lancet* 387, 1531-1539 (2016).
9. Araujo, L. M., Ferreira, M. L. & Nascimento, O. J. Guillain-Barre syndrome associated with the Zika virus outbreak in Brazil. *Arq Neuropsiquiatr* 74, 253-255 (2016).

Nguyen et al. (*Int. J. Mol. Sci.*, 2019, 20:3464)
Pang et al. (*J. Clin. Microbiol.*, 2017, 55:3339-3349)
Mustafa et al. (*Med. J. Armed Forces India*, 2015, 71:67-70)
Parkash et al. (*Viruses*, 2015, 7:5410-5427)
Muller et al. (*J. Infect. Dis.*, 2017, 215(Suppl 2):589-595)
Fatima et al. (*Pak. J. Pharm. Sci.*, 2015, 28:271-280)
Huhtamo et al. (*J. Clin. Virol.*, 2010, 47:49-53)

We claim:

1. A method for treating a Flavivirus infection in a human or non-human mammalian subject, said method comprising administering an effective amount of a compound to the subject having the Flavivirus infection, wherein the compound is colchicine, a prodrug of colchicine, a metabolite of colchicine, or a pharmaceutically acceptable salt of any of the foregoing, and wherein the Flavivirus infection is dengue virus infection or Zika virus infection.

2. The method of claim 1, wherein the Flavivirus infection is dengue virus infection.

3. The method of claim 1, wherein the compound is administered to the subject orally, nasally, rectally, parenterally, subcutaneously, intramuscularly, or intravascularly.

4. The method of claim 1, further comprising administering an additional agent to the subject, for treating the Flavivirus infection, or a symptom thereof, in the same formulation as the compound, or in a separate formulation before, during, or after administration of the compound.

5. The method of claim 1, wherein the compound is administered to the subject in a pharmaceutical composition that further comprises a pharmaceutically acceptable carrier or diluent.

6. The method of claim 1, wherein the Flavivirus infection is Zika virus infection.

7. The method of claim 1, wherein the compound is colchicine or a pharmaceutically acceptable salt thereof.

8. The method of claim 1, wherein the compound is colchicine or a pharmaceutically acceptable salt thereof, and wherein the Flavivirus infection is dengue virus infection.

9. The method of claim 1, wherein the compound is colchicine or a pharmaceutically acceptable salt thereof, and wherein the Flavivirus infection is Zika virus infection.

10. The method of claim 1, wherein the subject is human, wherein the compound is colchicine or a pharmaceutically acceptable salt thereof, and wherein the Flavivirus infection is dengue virus infection.

11. The method of claim 1, wherein the subject is human, wherein the compound is colchicine or a pharmaceutically acceptable salt thereof, and wherein the Flavivirus infection is Zika virus infection.

12. A method for inhibiting Flavivirus infection in human or non-human mammalian cells in vitro or in vivo, said method comprising contacting an effective amount of a compound to the human or non-human mammalian cell in vitro or in vivo after exposure of the cell to the Flavivirus, wherein the compound is colchicine, a prodrug of colchicine, a metabolite of colchicine, or a pharmaceutically acceptable salt of any of the foregoing, wherein the Flavivirus is dengue virus or Zika virus, and wherein the Flavivirus infection is dengue virus infection or Zika virus infection.

13. The method of claim 12, wherein the Flavivirus is dengue virus, and wherein the Flavivirus infection is dengue virus infection.

14. The method of claim 12, wherein the Flavivirus is Zika virus, and wherein the Flavivirus infection is Zika virus infection.

15. The method of claim 12, wherein the compound is colchicine or a pharmaceutically acceptable salt thereof.

16. The method of claim 12, wherein the compound is colchicine or a pharmaceutically acceptable salt thereof, wherein the Flavivirus is dengue virus, and wherein the Flavivirus infection is dengue virus infection.

17. The method of claim 12, wherein the compound is colchicine or a pharmaceutically acceptable salt thereof, wherein the Flavivirus is Zika virus, and wherein the Flavivirus infection is Zika virus infection.

18. The method of claim 12, wherein the cell is a human cell, wherein the compound is colchicine or a pharmaceutically acceptable salt thereof, wherein the Flavivirus is dengue virus, and wherein the Flavivirus infection is dengue virus infection.

19. The method of claim 12, wherein the cell is a human cell, wherein the compound is colchicine or a pharmaceutically acceptable salt thereof, wherein the Flavivirus is Zika virus, and wherein the Flavivirus infection is Zika virus infection.

* * * * *